(12) United States Patent
Bigalke

(10) Patent No.: US 6,845,676 B2
(45) Date of Patent: Jan. 25, 2005

(54) CONTINUOUS FLUID SAMPLER AND METHOD

(76) Inventor: Darrell Lee Bigalke, 11395 Irish Ave. North, Stillwater, MN (US) 55082

( * ) Notice: Subject to any disclaimer, the term of this patent is extended or adjusted under 35 U.S.C. 154(b) by 0 days.

(21) Appl. No.: 10/022,294

(22) Filed: Dec. 14, 2001

(65) Prior Publication Data

US 2003/0110870 A1 Jun. 19, 2003

(51) Int. Cl.[7] .............................. G01N 1/14; G01N 1/20
(52) U.S. Cl. ................................ 73/863.85; 73/863.03; 73/863.83; 73/863.86
(58) Field of Search ....................... 73/863.83–863.86, 73/863.03, 863.02, 864.34, 864.35

(56) References Cited

U.S. PATENT DOCUMENTS

| | | | | |
|---|---|---|---|---|
| 3,534,613 A | * | 10/1970 | Traver et al. | 73/863.85 |
| 3,776,042 A | * | 12/1973 | Werra et al. | 73/863.85 |
| 3,779,082 A | * | 12/1973 | Galloway | 73/863.85 |
| 4,785,676 A | * | 11/1988 | DeOca et al. | 73/863.85 |
| 4,941,517 A | | 7/1990 | Galloway | 73/863.85 X |
| 5,049,492 A | * | 9/1991 | Sauer et al. | 73/863.85 X |
| 5,086,813 A | | 2/1992 | Galloway | 73/863.85 X |
| 5,119,473 A | | 6/1992 | Ikenoue | |
| 5,269,350 A | | 12/1993 | Galloway | 141/1 |
| 5,296,197 A | * | 3/1994 | Newberg et al. | 73/863.85 X |
| 5,743,209 A | | 4/1998 | Bazin et al. | 119/14.08 |
| 5,803,078 A | * | 9/1998 | Brauner | 128/207.14 |
| H1960 H | * | 6/2001 | Conrad et al. | 73/864.82 |

FOREIGN PATENT DOCUMENTS

| | | | | |
|---|---|---|---|---|
| WO | WO 96/03859 | | 2/1996 | A01J/5/017 |
| WO | WO 00/33901 | * | 6/2000 | 604/93 |

OTHER PUBLICATIONS

"Keofitt World Leaders in Sterile Sampling", 4 pages (date unknown), but by Dec. 13, 2001.

Liquid Sampling Systems, Inc., Cedar Rapids, IA, "The Pro–Rata™ Line Sampler, The future of dairy sampling–today", 4 pages, (date unknown), but by Dec. 13, 2001.

Tate, J.L., "The Art of Managing Contamination", *Pharmaceutical Processing*, 4 pages (Jan. 2000).

* cited by examiner

*Primary Examiner*—Thomas P. Noland
(74) *Attorney, Agent, or Firm*—Merchant & Gould P.C.

(57) ABSTRACT

An aseptic, continuous sampling arrangement used in a fluid transportation system, the arrangement including an elbow pipe and a septum cartridge. The sampling arrangement further including a needle, a tube, and a collection reservoir, arranged such that the collection reservoir is in fluid contact with the fluid transportation system. The sampling arrangement configured to create a non-laminar fluid flow region from which a continuous sample of fluid material is drawn.

16 Claims, 5 Drawing Sheets

CONTINUOUS FLUID SAMPLER AND METHOD

FIELD OF THE INVENTION

This disclosure concerns a sampling arrangement. More specifically, this disclosure describes the assembly and method of use of a sampling arrangement for aseptic, continuous sampling of a fluid material.

BACKGROUND OF THE INVENTION

There are numerous applications wherein it is desirable to obtain discrete or continuous samples from fluid transportation systems or fluid processing enclosures. Enclosures and fluid transportation systems, as used herein, refer to any closed containment structure without respect to its size. Thus it includes such small enclosures such as cans that may be used in shipping starter bacteria from a culture lab. On the other end of the spectrum, it includes large tanks and associated pipelines, which may have capacities of several thousand gallons, such as are used in the dairy processing industry.

Efficient and effective techniques and apparatus for obtaining aseptic samples from such systems and enclosures, are particularly desirable. Examples of industries that require such aseptic sampling include, but are not limited to, the pharmaceutical, bioengineering/biotechnology, brewing/distilling, food processing and dairy processing industries. Applications for such samplings range broadly from process monitoring to laboratory and research applications. For example, sampling is commonly used on dairy farms for herd management or in regulated manufacturing facilities. The sampling is used to detect and control microbial contamination, spoilage microorganisms, foodborne illness, and environmental mastitis both within systems being sampled and externally of such systems. While preferred embodiments of this invention will be described with respect to its sampling use and application in the dairy industry, it will be understood that the invention is not to be construed as limited to use in that industry or to the application described, or to any limitations associated with the specifics of the components or methods disclosed with respect to such preferred embodiments.

Various methods and devices have been employed to perform sampling tasks. Typical sampling techniques commonly involve discrete or isolated sampling from a laminar portion of a fluid transport line. Typical such sampling systems and techniques that have been used in the dairy processing industry are described in U.S. Pat. Nos. 4,941,517; 5,086,813; and 5,269,350. To the extent that such patents may be used to assist the reader in understanding principles and examples of sampling apparatus and methods, they are herein incorporated by reference.

While the apparatus and techniques described in these patents are particularly applicable to systems designed to accommodate them, there also exists a need to perform sampling in existing enclosures and fluid transportation systems that have not been designed for sampling functions. Such systems typically require redesign or retrofitting to accommodate sampling functions. Such retrofitting can be expensive and/or difficult to achieve, can require significant system downtime in implementation of the sampling function and/or replacement of parts to maintain the system, or can lead to system degradation or contamination of the system being sampled. For example, one known method of discrete sampling of fluid involves inserting a needle through a sealing gasket located between connecting ends of pipelines of the fluid transportation system. Problems arises from this method as this method is not aseptic because the gasket becomes so perforated after repeated sampling that the gasket may lose its sealing integrity or introduce contaminants into the system though the perforations. This method requires that the gasket be replaced, which can become expensive both in labor costs and shut down costs.

There are many applications wherein it is desirable to obtain a continuous sample from fluid transportation systems or fluid processing enclosures. The discrete sampling methods typically extract a discrete sample size limited to the volume of a hypodermic needle and syringe. Typically the needle is inserted, fluid is drawn, and the needle is removed. It would be beneficial in some applications to have a system that could draw a continuous, controlled and constant sample volume over an extended period of time. A sampling device that facilitates this feature would also need to accommodate larger volume samples and a means to cool the sample during longer sampling time periods. While continuous sampling techniques have been tried, they have generally not been particularly effective, efficient or reliable in maintaining the aseptic condition of the system during the sampling interval.

Known discrete sampling techniques have not proven to be readily adaptable to continuous sampling techniques. For example, if the sample is taken from a region of laminar fluid flow, the sampling needle can create a venturi effect in the fluid flow being sampled, which can cause reverse flow siphoning from the collected sample and back into the sampled fluid. If such suction effect is disrupted by providing the sampling system with an air gap, the aseptic nature of the sampling system is compromised.

Improvement in methods and devices for sampling is needed, generally to better accommodate: ease of repeated continuous sampling of large volumes; structural integrity of fluid transport equipment; management of contamination; and convenience of continuous and controlled volume sampling. The present invention addresses these and other needs for continuous sampling of fluid transportation systems or fluid processing enclosures.

SUMMARY OF THE INVENTION

The present invention provides an efficient, effective and reliable assembly and method for aseptic continuous sampling of a fluid material. The principles of this invention can be simply implemented with readily available materials and techniques that enable application of the invention to sampling equipment of original design, as well as to relatively simple and inexpensive retrofitting of existing fluid enclosures or fluid transportation systems. The principles of this invention can readily be implemented in kit form for retrofitting applications. Further, replacement of expendable parts for maintaining the sampling system can be readily and inexpensively achieved without costly system down time and by minimizing contamination to the sampled system.

In one aspect of the invention, the disclosure describes a continuous sampling arrangement including a collection container, a connecting conduit in closed fluid communication with the collection container, a collector in fluid communication with the connecting conduit, a pipe elbow having an aperture, and a septum positioned within the pipe aperture. The septum is constructed to provide for penetration of the needle to facilitate fluid communication between the pipe elbow and the collection container.

In another aspect of the invention, the disclosure describes a continuous sampling arrangement configured to create a non-laminar flow area from which a continuous sample is drawn. A septum is placed adjacent the non-laminar flow area to facilitate penetration of a needle into the non-laminar flow area and provide fluid communication between the non-laminar flow area and a collection container.

In yet another aspect, a method for aseptic continuous sampling is disclosed wherein the principles described herein in a variety of embodiments are used in aseptic processes of sampling fluids.

In still another aspect, the invention relates to a kit that retrofits to existing fluid transportation systems or enclosures to permit aseptic continuous sampling according to the principles disclosed.

BRIEF DESCRIPTION OF THE DRAWINGS

Referring to the drawings wherein like numerals represent like parts throughout the several views.

DETAILED DESCRIPTION

Figure 1:
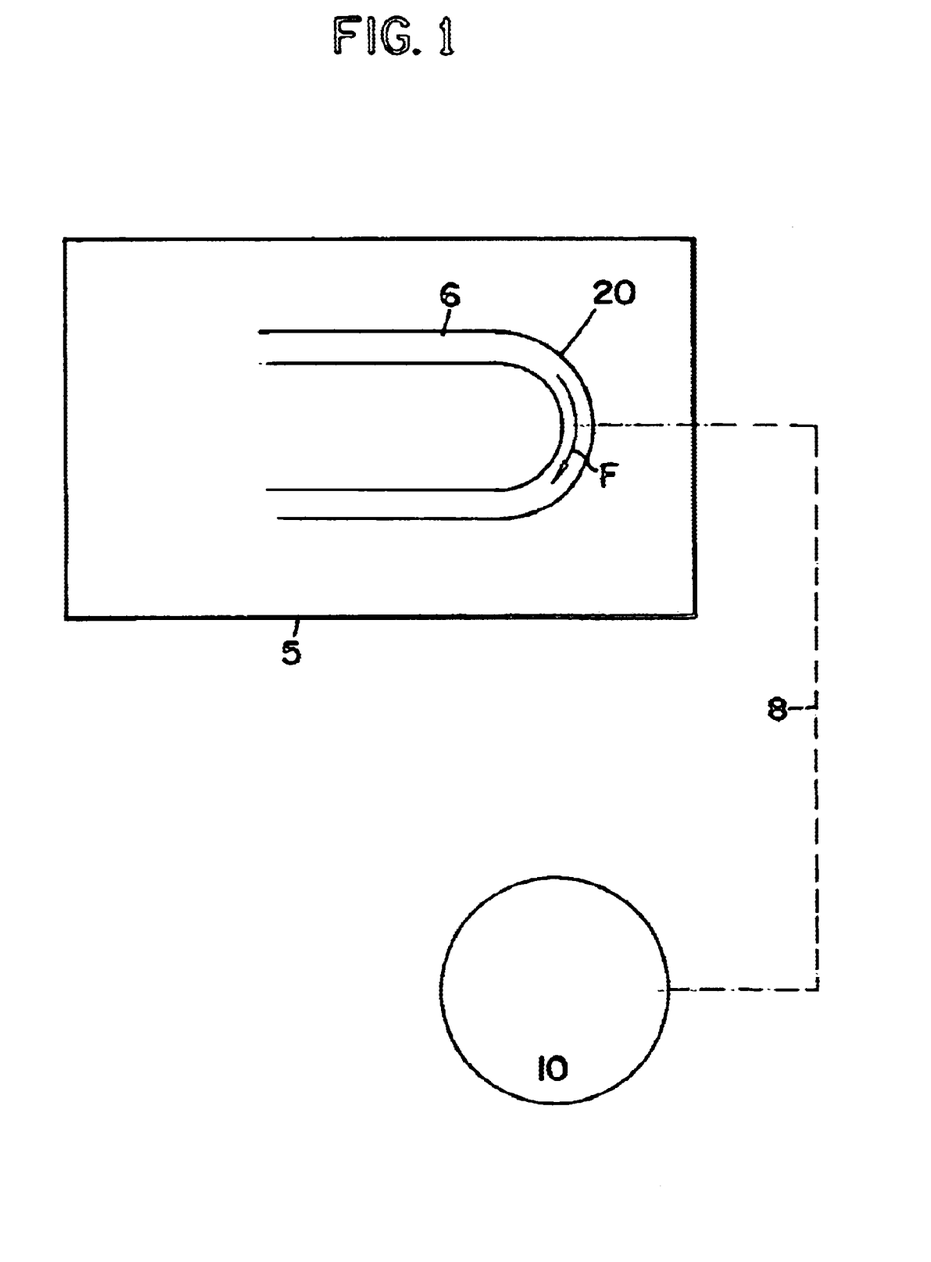
FIG. 1 is a schematic illustration of a system incorporating a continuous sampling arrangement in accordance with the principles disclosed.

This invention provides an apparatus and method for the continuous aseptic sampling of fluid material from a fluid transportation system or fluid processing enclosure 5, schematically illustrated in FIG. 1. A fluid material 6 to be sampled is illustrated as flowing through a fluid line 20 by the fluid flow arrow designation "F". A preferred sampling arrangement of the present invention is schematically illustrated at 10 and is depicted as operatively connected, by the dashed line 8, to sample the fluid material 6 (as hereinafter described in more detail).

The principles described herein for the sampling arrangement 10 can be used in various industries and in various applications where aseptic sampling of material is desired. Aseptic sampling involves transferring fluids to or from process systems that are sensitive to contamination from the outside environment. For example, the pharmaceutical, bioengineering/biotechnology, brewing/distilling, food processing and dairy processing industries are in need of aseptic sampling technology. Such sampling technology can be applied broadly, the applications ranging from process monitoring to laboratory and research applications. For example, the fluid processing enclosure or fluid transportation system 5 illustrated in FIG. 1 may comprise a dairy processing system used in the dairy industry. An example of one type of fluid processing enclosure or fluid transportation system 5 that has been used in the dairy processing industry is described in U.S. Pat. No. 5,269,350 and herein incorporated by reference. In such a system, the fluid material 6 therein may include raw milk or a processed milk product. The sampling arrangement 10 may be incorporated or retrofitted to the fluid transportation system 5 to provide continuous aseptic sampling for detecting microbial contamination or monitoring mastitis, coliform, food-borne illness bacteria, or spoilage bacteria in a dairy herd, for example.

While preferred embodiments of this invention will be described with respect to its sampling use and application in the dairy industry, it will be understood that the invention is not to be construed as limited to use in that industry or to the particular application described.

The Structural Components, Generally.

Figure 2:
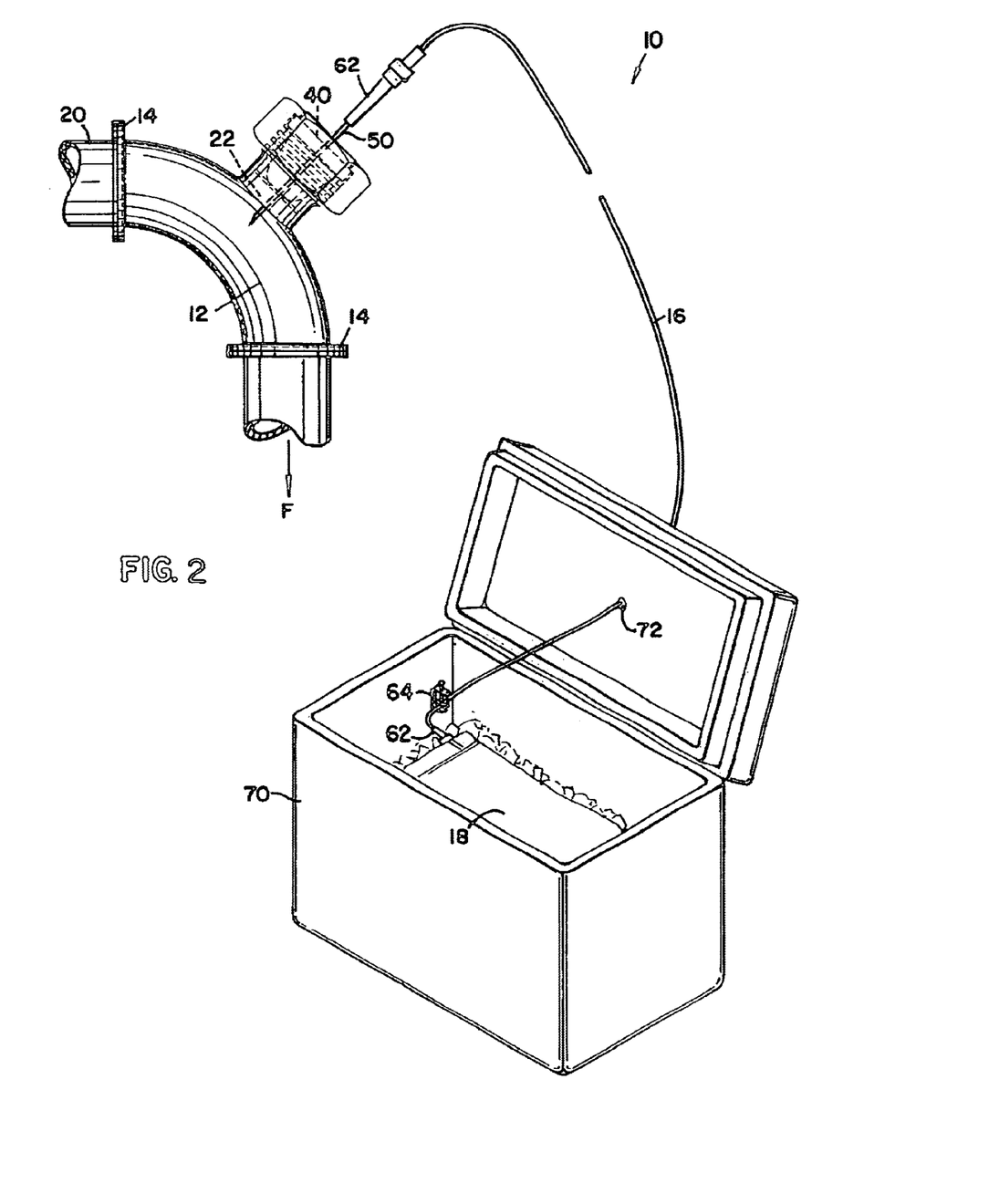
FIG. 2 is a detailed schematic illustration of one embodiment of the continuous sampling arrangement in accordance with the principles disclosed.

Referring to FIG. 2, the preferred sampling arrangement 10 depicted includes: an elbow 12 having flanges 14 and a port 22; a least one septum or septum cartridge 40 (shown in phantom); a connecting conduit 16; and a collection container 18. In general, the sampling arrangement 10 comprises an arrangement that provides for a continuous draw of fluid from a flow F within a fluid line 20, and deposits the fluid sample in the collection container 18 to provide the user with an accumulated process sample. It is to be understood that the fluid line 20 may comprise a variety of fluid transportation systems or fluid containment enclosures, and is not limited to pipe constructions. The collection container 18 may include a pouch, bag, reservoir, or other closed container of a typical construction and size, such as those used in the medical industry. In the illustrated embodiment, a medical type bag comprising a 2-liter collection pouch or bag is used. A variety of sizes and constructions of containers is contemplated.

As illustrated, the pipe segment or elbow 12 of the sampling arrangement 10 is in direct fluid communication with the fluid line 20 of the fluid transportation system. In accordance with the principles of the present invention, it is desirable to perform sampling from an area or region of non-laminar flow within the line 20. The elbow 12 provides a turbulent or non-laminar flow region within its interior flow cavity by its non-linear configuration. It is to be understood that there are other means of creating a non-laminar flow region within the fluid flow line, such as having a protrusion or device extending into the flowing fluid within a substantially straight portion of the fluid line. Therein fluid turbulence or non-laminar flow is formed downstream of the extending device or protrusion. Creation of a non-laminar sampling region eliminates the problem of reversed fluid flow from the sample to the main fluid line, which commonly occurs in devices and methods of the prior art.

Figure 3:
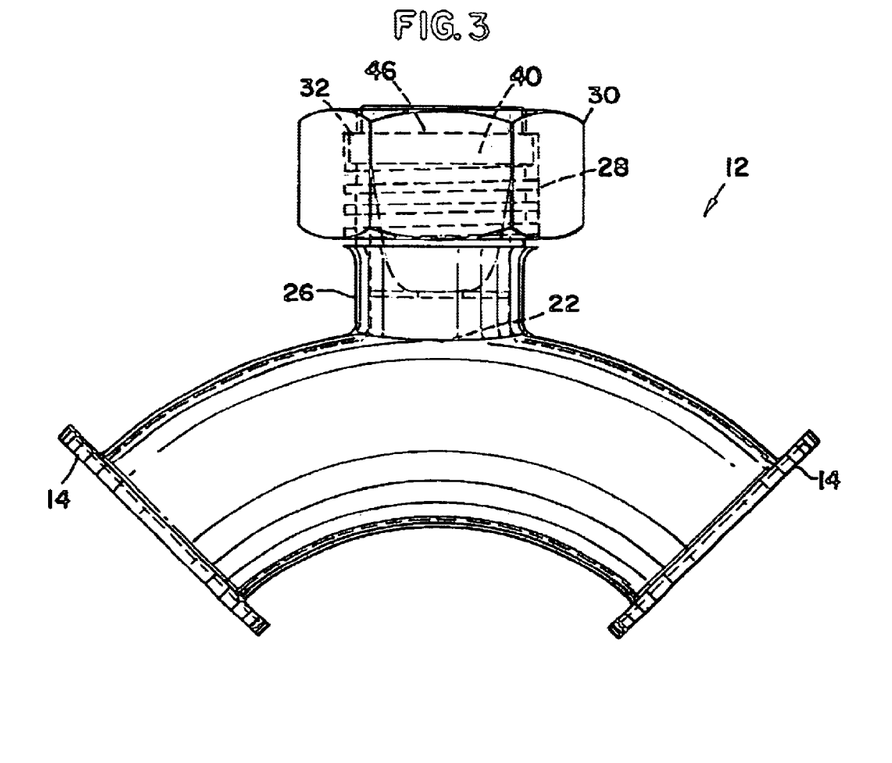
FIG. 3 is a side view of a pipe elbow depicted in the sampling arrangement of FIG. 2.
Figure 4:
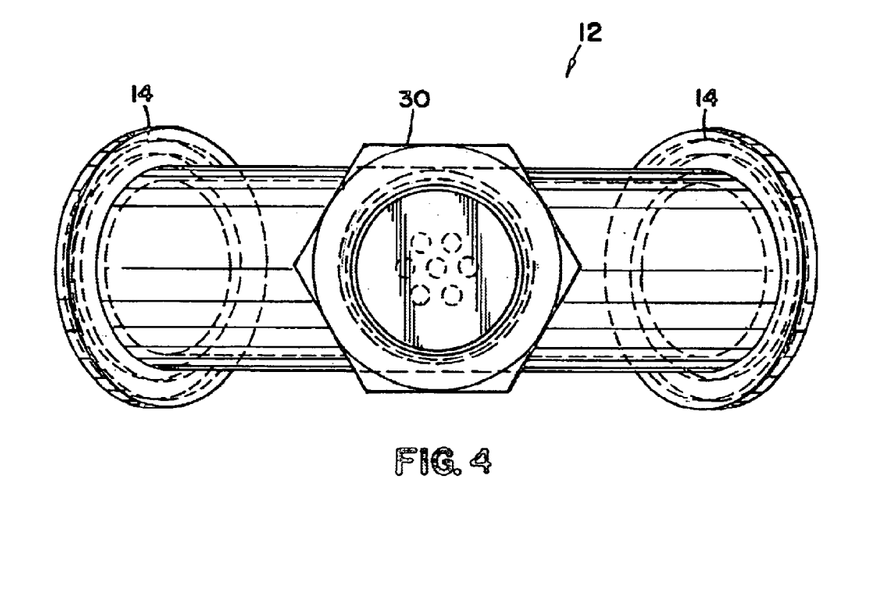
FIG. 4 is a top view of the pipe elbow depicted in FIG. 3.

Referring now to FIGS. 3 and 4, the connection flanges 14 of the elbow 12 extend circumferentially at each end of the elbow 12. The flanges 14 may include grooves (shown in phantom) sized to receive sealing gaskets (not shown) to seal the connections between pipe segments when installed in common fluid transportation line systems. In accord with the principles of the present invention, the sampling arrangement is generally adapted to be retrofit within existing fluid lines of various fluid flow systems 5 (FIG. 1). Certainly the sampling arrangement 10 can be incorporated as original equipment into new installations of fluid transportation lines as well. Other means of connection or retrofit adaptation, including welding, are contemplated as a means of installation. The sampling arrangement is generally designed with standard plumbing components to facilitate retrofit modifications. It is to be understood that non-standard elements, such as non-standard pipe diameter, fittings, or material, are within the scope of the principles disclosed.

Preferably the elbow 12 is made of industry standard stainless steel, such as 304 or 316L stainless steel. Other materials applicable for use in the industry into which the sampling arrangement is implemented are contemplated. The elbow depicted in FIG. 3 incorporates a standard 90-degree elbow. The angular configuration of the elbow will typically be a standard dimension within the range of 35 degrees to 180 degrees, typically 90 degrees. The preferred diameter of the elbow pipe is at least 1 inch, typically from about 1.5 to 3.5 inches in diameter.

The elbow 12 according to the present invention includes at least one aperture or port 22. The elbow 12 may be located in any configuration in the fluid transportation system where the port 22 is operably in fluid communication with the fluid material 6 within the system. Thus, the interior angle of the elbow 12 may be oriented, for example, upward, downward or sideways in a fluid line arrangement. It is also contemplated that to ensure that the port is operably in fluid communication with the fluid material 6, the port 22 may be configured in alternative locations on the elbow 12. In the illustrated embodiment, the port 22 is located on the outer radius of the elbow 12. Alternative embodiments may include, for example, an elbow having a port located on the interior radius of the elbow. Preferably, the port 22 is disposed at or within a non-laminar flow region of the elbow 12.

As depicted in FIG. 3, the port 22 may include a transversely extending pipe portion or conduit 26. The conduit 26 is sized to receive a septum cartridge 40. The conduit 26 may include an externally threaded region 28 for purposes of securing the septum cartridge 40. In one embodiment, the thread comprises a standard 1.5"-8 ACME thread corresponding to a mating internally threaded nut 30. The threaded nut 30 may include an internal annular shoulder 32 (shown in phantom). The annular shoulder 32 acts as a bearing surface that engages a first surface 46 of the septum cartridge 40 (shown also in FIG. 7) to secure the septum cartridge in sealing manner when assembled within the port 22. Other types of fasteners commonly used as securing or retaining means within this context are contemplated and may include, for example, a hex nut, a knurled lock nut, or a keyed nut.

Figure 5:
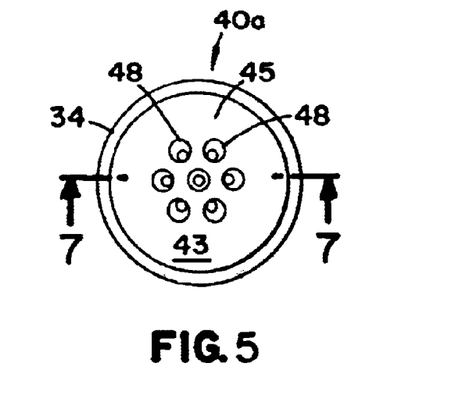
FIG. 5 is a top view of one embodiment of a septum used in the sampling arrangement of FIG. 2.
Figure 6:
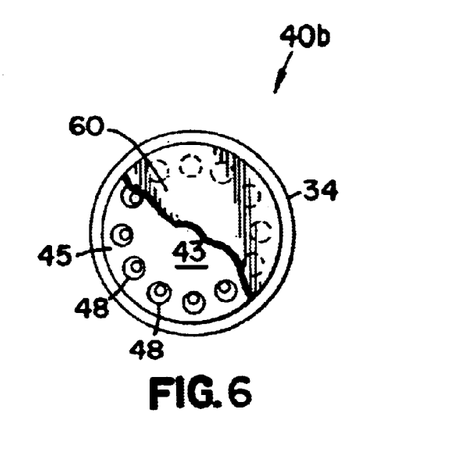
FIG. 6 is a top fractional view of another embodiment of a septum used in the sampling arrangement of FIG. 2.
Figure 7:
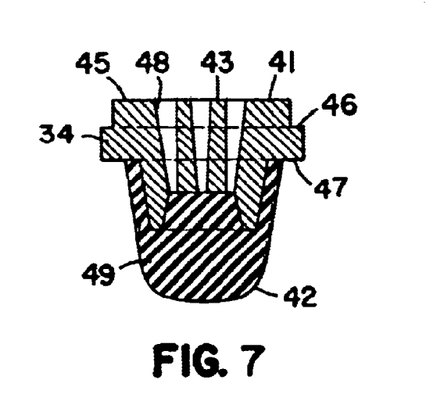
FIG. 7 is a cross sectional view of the septum shown in FIG. 5, taken generally along line 7—7 of FIG. 5.

Referring generally to FIG. 2, the septum cartridge 40 is in fluid communication with the interior cavity of the fluid line 20 by means of the aperture or port 22 in the elbow 12. As shown in FIGS. 5–7, the septum cartridge 40 generally comprises a cap 45, a central core member or boot 49, and a plurality of guide holes 48 formed through the cap. For purposes of clarifying features, the septum cartridge 40 can be considered to have a top 41 and a bottom 42.

The cross-section of the boot 49 is seen to increase progressively from the bottom 42 toward the top 41 of the septum cartridge 40. The boot 49 is sized such that when the boot is placed within the port 22 of the elbow there is compressive contact between the interior surfaces defining the port 22 and the boot 49. The boot thereby functions as a sealing member. The boot 49 illustrated is generally conical, but could adopt a variety of shapes as will be obvious from the following discussion of the functioning of the septum cartridge in combination with other components of the invention.

The boot 49 may be made of material that is generally considered to be of a rubber compound. While compounding of an acceptable rubber composition is believed to be within the skill of the rubber molding art, it is found that rubber compounds based on ethylene propylene diene monomer terpolymer (EPDM) are particularly advantageous, having suitable sealing characteristics. EPDM is a known elastomer, and recognized by those skilled in the polymer arts. Other elastomers are contemplated, such as those derived from, or modified with, butene isoprene, ethylene, and the like. In an alternative embodiment, the boot may comprise a silicon compound. Silicon also provides suitable sealing characteristics. Materials such as Viton or other FDA approved elastomers are also contemplated for use in manufacture of the boot.

Preferably, the cap 45 includes an annular radially extending portion 34 defining the first upwardly oriented surface 46 and an opposing second lower surface 47. The outer diameter of the annular portion 34 is preferably only slightly less than the inner diameter of the internal shoulder 32 on the threaded nut 30 for purposes of engaging and retaining the septum cartridge 40 within the port 22 of the elbow in the sampling arrangement 10.

The cap 45 is made of a material that is normally not penetrable by conventional hypodermic needles. A typical material for fabrication of the cap may include one of the engineering plastics, such as nylon, polypropylene, or high-density polyethylene. The penetrability of the septum cartridge 40 is thus provided by one or more of the integrally formed guide holes 48, which begin from a top surface 43 of the cap 45 and extend downwardly through the cap 45.

The guide holes 48 are integral with the cap 45 and located to correspond to the boot 49. The guide holes 48 extend downwardly through the cap structure 45 and are oriented and positioned so that a sampling needle 50 (shown in FIG. 8) may pass through the guide hole 48 and into the boot 49. The guide holes 48 are generally sized to be only slightly larger than the needle, such that the needle slidably fits snugly within the guide hole, preferably without substantial friction, but with a close enough fit to ensure that the guide hole provides direction to the needle as it is inserted through the boot. In one embodiment (FIG. 5), the septum cartridge 40a includes seven guide holes. In another embodiment (FIG. 6), the septum cartridge 40b includes twelve guide holes. Typically the septum cartridge includes at least one guide hole, generally 1 to 15 guide holes.

A cover film 60 covers the top surface 43 of the cap 45, including the guide holes 48 formed in the top surface 43 of the cap 45. The cover film 60 easily identifies used holes to reduce the risk of contamination from reinserting a needle into a previously used guide hole. The cover film 60 may be made from any readily pierceable film material. A typical film material is a vinyl tape having an adhesive coating to securably attach the cover film 60 to the top surface of the cap 45.

Figure 8:
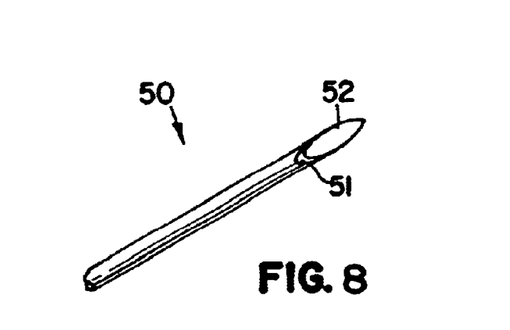
FIG. 8 is a fragmentary perspective view of a needle depicted in the sampling arrangement of FIG. 2.

Referring to FIGS. 2 and 8, the penetrating body or needle 50 is in fluid communication with the connecting conduit 16, and the connecting conduit 16 is in fluid communication with the collection container 18. In the preferred embodiment, the needle comprises a beveled end 51 having an aperture 52 that defines a hollow portion running longitudinally through the needle 50. It is to be understood that other penetrating bodies, such as lumens, hollow members, or inserting devices may be used in accordance with the principles disclosed.

In use, the needle 50 penetrates the cover 60, passes through a selected guide hole 48, and penetrates through the boot 49. As the needle penetrates the boot, the needle displaces the elastomeric/rubber material of the boot which forms a fluid impenetrable seal about the needle. The beveled end 51 of the needle 50 progresses through the boot 49 and emerges from the boot at the bottom 42 of the septum cartridge 40. The needle therein enters into the flow of fluid F.

The needle 50 is sized and adapted for use with the septum cartridge 40. Typically the needle comprises a 12 gauge to 22 gauge needle, preferably a 16 gauge needle. The needle generally has a length of from about 1.0 inches to 4.5 inches. Preferably the needle is at least 1.5 inches in length if the port 22 is bottom placement oriented and at least 2.0 inches if the port 22 is top placement oriented. What is meant by top and bottom placement oriented is how the sampling port is oriented with respect to ground. Thus, if the elbow is top placement oriented, a longer needle 50 is needed to ensure the needle aperture 52 is submerged within the fluid material when operatively inserted through the septum 40.

Still referring to FIG. 2, the connecting conduit 16 also includes sealing ends 62 at locations where the fluid flow transitions from the needle 50 to the connecting conduit 16 and from the connecting conduit 16 to the collection container 18. A typical, usable connecting conduit is the type used by the medical industry in fluid administration sets. Conduit in accordance with the principles disclosed includes, for example, tubing, flexible piping or flexible lumen constructions that provide closed, aseptic fluid communication between ends.

Preferably the connecting conduit 16 is of sufficient length to reach from the elbow 12 to an area where the collection container 18 is placed. The length may thus vary and typically falls within the range of 5 inches to 65 inches, and preferably is about 38 inches in length. In one embodiment, the connecting conduit comprises a 0.121 inch inside diameter and a 0.166 outside diameter. It is to be understood that typical fluid administration sets having a needle, connecting conduit, and a collection pouch are contemplated for use in this sampling arrangement.

In use, the needle 50 is inserted through the septum 40 into a non-laminar fluid flow region of the elbow 12. Sampling at a non-laminar fluid flow region addresses the problem of reversed fluid flow often created by a venturi effect of prior sampling systems. The venturi effect is created where the velocity of the laminar fluid flow flowing past an orifice or tube opening (such as in a needle) causes a corresponding decrease in fluid pressure, which creates a siphoning or suction. Thus, instead of drawing sampled fluid from the fluid line into a collection container, sampled fluid is actually drawn from the collection container back into the fluid line. The sampling arrangement 10 of the present invention reduces or eliminates this problem.

Some Selected Alternate Embodiments

Figure 9:
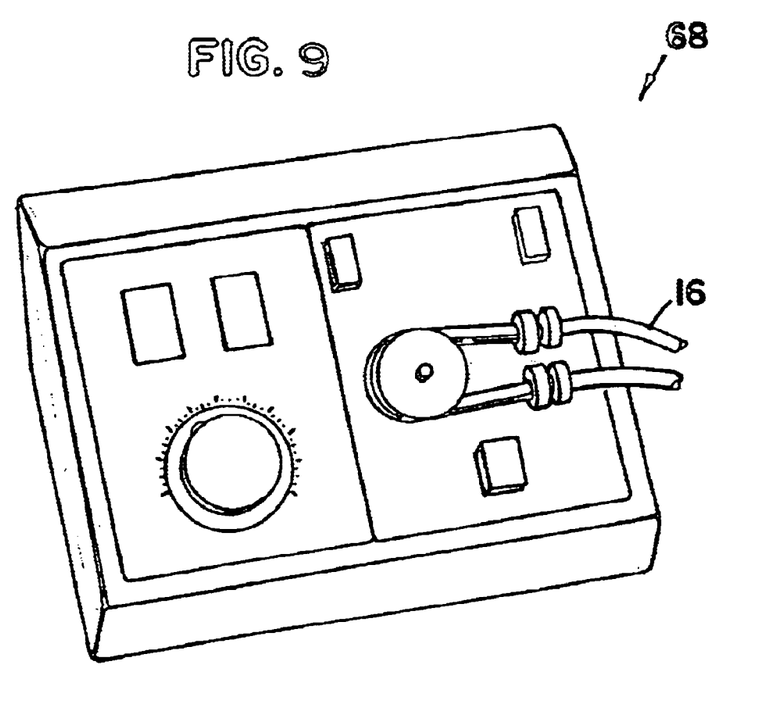
FIG. 9 is an illustration of one embodiment of a regulating device that can be used in the sampling arrangement of the present invention.

Alternative embodiments incorporating the principles of the present invention will be apparent from the description below and in the context of the illustrations in FIGS. 2 and 9.

In one alternative embodiment, the sampling arrangement 10 includes a flow restricting device. The flow restricting device may comprise a clamp 64 as shown in FIG. 2. The clamp 64 compressively engages the outer surface of the connecting conduit 16 and is adjustable such that flow through the tube may be restricted to a desired flow rate. Thereby, the continuous sampling rate may be increased or decreased during sampling as needed.

Another embodiment of the sampling arrangement includes an alternative means of regulating flow. FIG. 9 depicts a fragmented portion of a sampling arrangement including a metering or peristaltic pump 68. The peristaltic pump 68 cooperatively engages connecting conduit 16 and is adjusted as is known in the art to provide a desired regulated flow rate.

The clamp 64 and the peristaltic pump 68 are products of common manufacture. The clamp may comprise any clamping device suitable to provide restriction in the connecting conduit 16. The peristaltic pump may comprise, for example, a variable flow pump having a medium flow rate of 4.0 to 85.0 milliliters per minute. Specifically, a Medium Flow variable flow pump, Model Number 54856-075, manufactured by MASTERFLEX is one variable flow pump that may be used.

Yet another embodiment of the present invention provides for cooling of the extracted sample held by the collection container. If it is desirable to keep the extracted sample cool during collection, the collection container 18 may be placed in an insulated cooler 70 surrounded by ice or cold packs as shown in FIG. 1, for example. Common coolers can be modified to include a hole 72 in the top or lid through which the connecting conduit 16 can be routed.

The alternative embodiments herein described may be used in combination with each other or used independent of one another.

The Method of Continuous Sampling, Generally.

In operation, the elbow 12 is installed at a convenient sampling location along a fluid line 20. The elbow is preferably oriented such that the port 22 is in direct fluid contact with the material transferred within the fluid line, to reduce the potential of air drawn during sampling.

The boot 49 of the septum cartridge 40 is placed into the sampling port 22 until the second surface 47 of the cap 45 rests against the outer edge of the sampling port 22. The securing nut 30 is installed onto the conduit of the port 22 to sealingly, operatively secure the septum within the port.

For aseptic sampling, the sampling arrangement, including the port, nut, septum cartridge, etc, are sanitized with a common alcohol prep or other sanitizer. In particular, aseptic sampling is optimized when the cover film 60 is cleansed with a disinfectant, and a sterilized needle 50 is inserted through the disinfected cover film, through an unused guide hole, and through the septum boot.

The needle is preferably directed or slanted toward the center of the septum boot at insertion. This provides greater assurance that the needle penetrates through the entirety of the boot. In effect, the boot essentially squeegees or cleanses the needle of any contaminants missed during initial aseptic disinfectant processes. Directing the needle toward the center of the boot also reduces the possibility of contacting the wall of the extended portion of the elbow.

The needle may be oriented such that the beveled end 51 faces toward the flow of the fluid material to aid in fluid sampling. A pressure differential is applied between the collection container and the fluid line to effect the fluid sampling or material transfer. The pressure differential maybe applied in a number of ways. One way is by introducing pressure into the fluid line. Another is by reducing pressure in the connecting conduit or collection container. Any means of generating an adequate pressure differential between the fluid line and the collection container is effective to cause the flow of material through the needle. Other methods of applying the pressure differential and thus effecting the transfer of a sample will be obvious to those skilled in the art.

Material from a tank, for example, thus flows from the fluid line 20, through the needle 50, and into the collection container 18 by way of the connecting conduit 16. In one alternative application, the collection container may be placed into a cooling container 70 of ice or ice water, for example, to reduce or eliminate bacterial growth during the sampling process.

The flow from the fluid line 20 to the collection container 18 may be adjusted to a particular flow or sampling rate by means of the clamp restriction. The flow may likewise be metered wherein the peristaltic pump is assembled to the connecting conduit to regulate the flow.

When the desired sample has been collected, the collection container is removed from the connecting conduit 16 and sealed. The needle 50 is removed from the septum cartridge 40. As the needle end is withdrawn, the material of the boot 49 withdraws into the position held prior to needle penetration. The boot 49 of the septum 40 thus closes and seals the passageway of the now removed needle.

After performing a number of sampling procedures, so that all guide holes have been used, the septum cartridge 40 is removed and discarded. The punctured cover film 60 provides a ready indictor of those guide holes that have been used. A new septum cartridge easily replaces the used septum cartridge for future samplings.

The above specification, examples and data provide a complete description of the manufacture and use of the invention. Many embodiments of the invention can be made according to the disclosed principles.

I claim:

1. A continuous sampling arrangement, comprising:
   (a) a bag within which a sample is collected;
   (b) a tube being in fluid communication with the bag;
   (c) a needle in fluid communication with the tube;
   (d) an elbow pipe having an internal volume and an aperture, said elbow pipe being arranged and configured for operative connection to a closed fluid flow line from which a fluid sample is to be taken;
   (e) a removable septum positioned within the aperture, the septum constructed for penetration of the needle therethrough to provide fluid communication between the internal volume of the elbow pipe and the bag.

2. The sampling arrangement of claim 1, wherein the aperture is positioned adjacent to a non-laminar fluid flow region of the elbow pipe.

3. The sampling arrangement of claim 1, wherein the septum comprises:
   (i) a penetrable body;
   (ii) a cap piece in contact with at least a portion of the penetrable body; and
   (iii) a penetrable layer at least partially covering a portion of the cap piece.

4. The sampling arrangement of claim 3, wherein the penetrable body comprises a rubber construction.

5. The sampling arrangement of claim 3, wherein the penetrable body comprises a silicon construction.

6. The sampling arrangement of claim 3, wherein the penetrable body defines a volume of mass having a tapering diametric shape, the diameter proximate the cap piece corresponding to the diameter of the aperture of the elbow pipe.

7. The sampling arrangement of claim 3, wherein the septum includes an integral cap piece and penetrable body construction.

8. The sampling arrangement of claim 3, wherein the tubing is in fluid communication with the internal volume of the elbow pipe by insertion of the needle through the penetrable body of the septum.

9. The sampling arrangement of claim 3, wherein the cap piece includes a plurality of openings configured to guide the needle into the penetrable body of the septum during needle insertion.

10. The sampling arrangement of claim 9, wherein the plurality of openings is at least partially covered by the penetrable layer, the penetrable layer providing a visible indication of previously penetrated openings.

11. The sampling arrangement of claim 1 wherein the aperture includes an outwardly extended portion defining an internal diameter sized to receive the septum.

12. The sampling arrangement of claim 11 wherein the aperture further includes a male threaded section on the outwardly extended portion, and a threaded nut sized to cooperatively engage the male threaded section to secure the septum within the extended portion of the aperture.

13. The sampling arrangement of claim 1, wherein the elbow pipe includes coupling ends, each coupling end having a flange that further defines a groove to receive a sealing member, wherein the elbow pipe configuration is configured to retrofit within an existing fluid transportation system.

14. The sampling arrangement of claim 1, wherein the arrangement further includes a flow control device to regulate the fluid flow from the elbow pipe to the bag.

15. The sampling arrangement of claim 14, wherein the flow control device includes a clamp to restrict fluid flow to the bag.

16. The sampling arrangement of claim 14, wherein the flow control device includes a peristaltic pump to regulate fluid flow to the bag.

* * * * *